US006306346B1

United States Patent
Lindsay

(12) 
(10) Patent No.: US 6,306,346 B1
(45) Date of Patent: Oct. 23, 2001

(54) SELF-CONTAINED PACK ASSEMBLY FOR AN EXTRACORPOREAL BLOOD CIRCUIT

(75) Inventor: Erin J. Lindsay, Manchester, MI (US)

(73) Assignee: Terumo Cardiovascular Systems Corporation, Somerset, NJ (US)

( * ) Notice: Subject to any disclaimer, the term of this patent is extended or adjusted under 35 U.S.C. 154(b) by 0 days.

(21) Appl. No.: 09/244,426

(22) Filed: Feb. 10, 1999

(51) Int. Cl.[7] .............. A61M 1/14; A61M 1/34; A61M 37/00; B64D 47/00
(52) U.S. Cl. .......... 422/45; 604/4.01; 604/6.14; 604/6.15; 600/19; 261/DIG. 28
(58) Field of Search .................. 604/4–6, 4.01, 604/5.01, 6.01, 6.13–6.15; 422/44–48; 600/19; 261/DIG. 28; 333/202; 60/325

(56) References Cited

U.S. PATENT DOCUMENTS

| | | | |
|---|---|---|---|
| 4,083,777 | 4/1978 | Hutchisson | 210/22 |
| 4,149,635 | 4/1979 | Stevens | 206/370 |
| 4,370,983 | 2/1983 | Lichtenstein | 128/630 |
| 4,420,085 | 12/1983 | Wilson et al. | 206/571 |
| 4,436,620 | 3/1984 | Bellotti et al. | 210/90 |
| 4,479,761 | 10/1984 | Bilstad et al. | 417/395 |
| 4,479,762 | 10/1984 | Bilstad et al. | 417/395 |
| 4,765,959 * | 8/1988 | Fukasawa | 422/48 |
| 4,850,954 | 7/1989 | Charvin | 604/4 |
| 5,266,265 | 11/1993 | Raible | 422/46 |
| 5,476,444 | 12/1995 | Keeling et al. | 604/4 |
| 5,540,653 | 7/1996 | Schock et al. | 604/7 |
| 5,643,190 | 7/1997 | Utterberg | 604/4 |
| 5,750,025 | 5/1998 | Holmes et al. | 210/361 |
| 5,753,173 * | 5/1998 | Leonard et al. | 264/503 |
| 5,800,721 * | 9/1998 | McBride | 210/506 |
| 5,823,986 | 10/1998 | Peterson | 604/4 |
| 5,957,879 * | 9/1999 | Roberts et al. | 604/4 |
| 5,958,338 * | 9/1999 | Lindsay et al. | 422/45 |

OTHER PUBLICATIONS advertisement for "EASTAR Copolyester—Protect Your Treasures.", © 1998 Eastman Chemical Company, featured in *Pharmaceutical & Medical Packaging News*, Feb. 1999 edition.
Cobe Blue Ribbon Packs, "The World's Recognized Leader in Fully Integrated, Pre–Connected Bypass Circuits", pp. 1–2, http://www.cobecv.com/bluribbn.html.
Amsect Today, Jan. 1998, advertisement, "Fast Start. Smooth Finish. Introducing The Medtronic MicroCircuit", © 1997 Medtronic, Inc.
advertisement, "There's more to this package than meets the eye.", Cobe Blue Ribbon Pack; Cobe Cardiovascular.
advertisement, "With Cobe® Blue Ribbon Pack® Heart–Lung Circuits, there's much less hand movement.", Cobe Blue Ribbon Pack, Cobe Cariovascular.
Lonsky, et al., "How Long Can the Previously Assembled Cardiopulmonary Bypass Circuit Stay Sterile?", ACTA MEDCIA, vol. 41, pp. 91–93 (1998).

* cited by examiner

Primary Examiner—Angela D. Sykes
Assistant Examiner—Patricia Bianco
(74) Attorney, Agent, or Firm—Burns, Doane, Swecker & Mathis, LLP

(57) ABSTRACT

A self-contained pack assembly includes all of the disposable components of an extracorporeal support circuit for cardiac bypass surgery. The pack assembly comprises a blood reservoir, a blood oxygenator, and a carrier for vertically mounting the blood reservoir and blood oxygenator. Trays may be releasably attached to the carrier to serve as containers for coiled tubing used in the support circuit.

36 Claims, 9 Drawing Sheets

SELF-CONTAINED PACK ASSEMBLY FOR AN EXTRACORPOREAL BLOOD CIRCUIT

FIELD OF THE INVENTION

The invention relates to extracorporeal blood circuits for oxygenation and circulation of a patient's blood during cardiac bypass surgery, and in particular to a self-contained pack assembly that includes the tubing and other disposable components of an extracorporeal blood circuit

BACKGROUND OF THE INVENTION

During cardiac bypass surgery a patient's heart is slowed or stopped for surgical repair, and his or her blood must be artificially oxygenated and pumped through the body using an extracorporeal support circuit. Using this system, venous blood is diverted from entering the right chambers of the heart and is instead directed through a series of tubes, pumps and filters, which provide fresh oxygen to the blood and return it to the body's systemic circulation at the aorta. The oxygenated blood is then circulated throughout the body. The circuit thus ensures that the patient continues to be nourished by oxygenated blood flow while the heart is unable to function.

In performing such a procedure, a complicated apparatus is required. One or two blood reservoirs, an oxygenator (possibly combined with a heat exchanger), a blood pump, and multiple tubes to connect the various components are needed and must be assembled and arranged before surgery may begin. Typically a significant amount of time must be spent just prior to surgery to accomplish the set-up, and great attention must be paid to the details of this complicated task.

In a conventional extracorporeal support circuit, a venous line drains blood from the right side of the patient's heart and delivers it to a blood reservoir. The blood is then pumped by a specially designed pump from the outlet of the blood reservoir into a blood oxygenator for oxygenation and cooling. The oxygenated blood is artificially pumped via an arterial line to the venous line, and the circuit is continued in this fashion until the surgical repair is complete.

The support circuit normally includes a blood scavenging sub-circuit for recovering and recycling blood from the surgical field. The sub-circuit includes one or more suckers (typically two to four) for sucking blood from the surgical field. Vacuum is applied to the suckers by a peristaltic positive displacement pump (also known as a roller pump) or wall vacuum to deliver the scavenged blood to a cardiotomy reservoir. The reservoir includes a defoaming section to remove entrained air and a filter. The outlet for the cardiotomy reservoir delivers the de-foamed, filtered blood to the venous reservoir of the main circuit. Various cardiotomy reservoirs are described in U.S. Pat. Nos. 3,891,416, 3,993,461, 4,208,193 and 4,243,531. The cardiotomy reservoir may alternatively be an integral portion of the venous blood reservoir in which the scavenged blood flows through a filter section and the venous blood does not.

A schematic diagram of a conventional extracorporeal support system is shown in FIG. 1. A reservoir 20 is provided for cleaning, debubbling, and collecting the blood. A tubing assembling called a pump loop 22 includes a pump inlet line 24 and a pump outlet line 26. These two lines are connected to an arterial pump 28, which for the purposes of this invention will most conveniently be of the type which has a pump header 30 which is separable from the motor portion. The pump outlet 26 leads to the inlet of the oxygenator 32, which may include a heat exchanger 34.

The elements so far described are connected to the body of the patient by a tubing assembly called an A-V loop 36. The A-V loop 36 includes a venous line 38 to carry the patient's low-pressure, oxygen depleted venous blood to the reservoir, and an arterial line 40 carrying high-pressure, oxygen rich arterial blood from the oxygenator 32 back to the patient. It may be convenient to monitor the condition of the blood in these two lines, so a blood parameter monitor 42 may be provided having sensors 44 and 46, which are kept in chemical equilibrium with the blood flowing in the venous line 38 and the arterial line 40, respectively. A hematocrit monitor 48 may also be provided, having its own sensor 50, conveniently monitoring the blood in the venous line 38.

It may be convenient to perfuse the patient's heart directly with a different solution than is provided to the rest of the patient's body. Cardioplegia solution is typically used in this fashion to slow or stop the patient's heart during surgery. A cardioplegia pump 52 may be used to deliver cardioplegia solution supplied by solution line 56 from a solution supply 58. The cardioplegia pump outlet line 60 passes through a cardioplegia heat exchanger 62 and a bubble trap 64 before delivering cardioplegia solution to the heart at the cardioplegia catheter 66.

Two suction lines are typically provided to recapture blood from the site of the surgical incision that has escaped the closed system. The first is called the vent line 68, and runs from a vent catheter 70 through a vent pump 72 to the reservoir 20. The second is called the suction line 74, and runs from a suction device 76 through a suction pump 78 and once again to the reservoir 20.

To prepare the system for use, each of the tubing connections must be individually made by a skilled person in the operating room. Many of these connections are between disposable system components, such as tubes and filters, which could advantageously be pre-connected and assembled in an assembly pack for quick attachment to the nondisposable elements of the system, thus enhancing operating room efficiency. However, no such assembly packs have heretofore been developed in the art.

SUMMARY OF THE INVENTION

The invention provides an assembly pack that contains the major disposable components of an extracorporeal support circuit, conveniently packaged in ready-to-use condition. All the tubing needed to connect the patient for bypass surgery is included in the pack, with the necessary attachments between the various elements in the pack pre-made in a sterilized condition. In preparation for surgery, only a few connections must be made between the assembly pack and the nondisposable elements of the circuit compared to the numerous connections that were previously required. The assembly pack allows one to carry and mount all the disposable paraphernalia needed for perfusion with a single hand.

The pack assembly is built around a backbone called the carrier, which serves as a support and handle for the other components. Preferably, a reservoir and an oxygenator are both physically but releasably attached to this carrier. Disposed around these central components, and attached to them in some way, will preferably be at least one tray. In preferred embodiments, two trays will be present, and it is considered particularly convenient that each of these trays be releasably attached to both the carrier and the reservoir. The carrier preferably has a handle so that the pack assembly can be easily moved and manipulated after being removed from its shipping container.

In preferred embodiments, various tubing assemblies will be pre-attached to the reservoir and the oxygenator, with the majority of their lengths conveniently coiled and disposed within the trays. Most conveniently, the trays will themselves be divided into several compartments, and tubes that share some functional relationship will be packaged together in the same compartment, separated from other tubes with different functions.

In particular, in one preferred embodiment there is a prime line for priming the reservoir prior to surgery. This prime line conveniently has a priming tube attached to the reservoir at one end and a bag spike at the other end. The end with the bag spike is disposed within a first compartment in one of the trays. It is particularly convenient if that tray has a narrow cut-out portion to admit the free end of the prime line so that the prime line may be deployed and attached to a bag of saline solution without first detaching the tray. In some embodiments, it is convenient that one or more of the tubes will have a grommet, and that grommet will allow the tube to pass through the cut-out portion in the wall of the tray while maintaining a sterile seal.

In similar fashion, an A-V loop, a pump loop, and one or more suction lines will be present in a preferred embodiment, and each group of lines will be packaged with most of their lengths within their own individual compartment within one of the trays. In the most preferred embodiments cut-outs are provided within the side walls of the trays so that each line or group of lines may be deployed before the trays are detached and discarded.

In the most preferred embodiment the trays hang vertically in the pack assembly, and a cover sheet is provided for each tray in order to keep the components within it enclosed. Any moderately sturdy sheet material should be suitable for the purpose, but a film of transparent polymeric material is considered particularly preferred so that the components within the trays can be inspected visually after assembly.

In a preferred embodiment of the invention, the pack assembly will include a barrier pouch enclosing all of its components. In the most preferred embodiment, the pack assembly is "self-contained," meaning that all the tubing and disposable elements necessary to connect a patient for bypass surgery is included in the pack.

DETAILED DESCRIPTION OF THE INVENTION

During preparation for a surgical procedure requiring cardiac bypass, the pack assembly of the invention may be transformed from an undeployed configuration to a deployed configuration and used as part of an extracorporeal circuit. In the undeployed configuration, all of the disposable components of the extracorporeal circuit are either attached to a carrier or contained within a sealed tray associated with the carrier. To deploy the pack assembly for use, the trays are removed from the pack assembly and opened, and the various pre-attached lines are uncoiled and positioned in their appropriate positions in the operating room.

Figure 1:
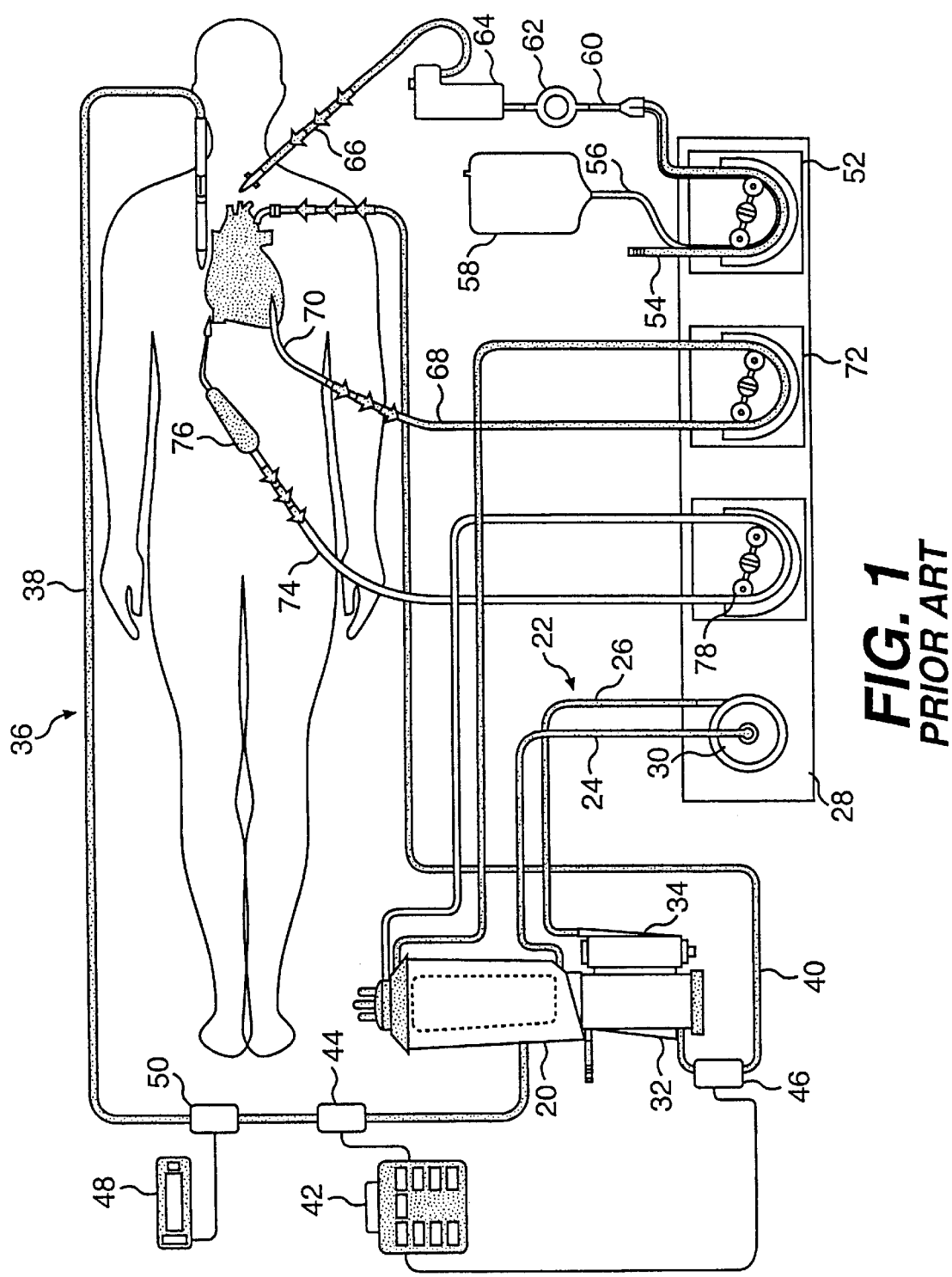
FIG. 1 is a schematic diagram showing a prior art extracorporeal support circuit.
Figure 2:
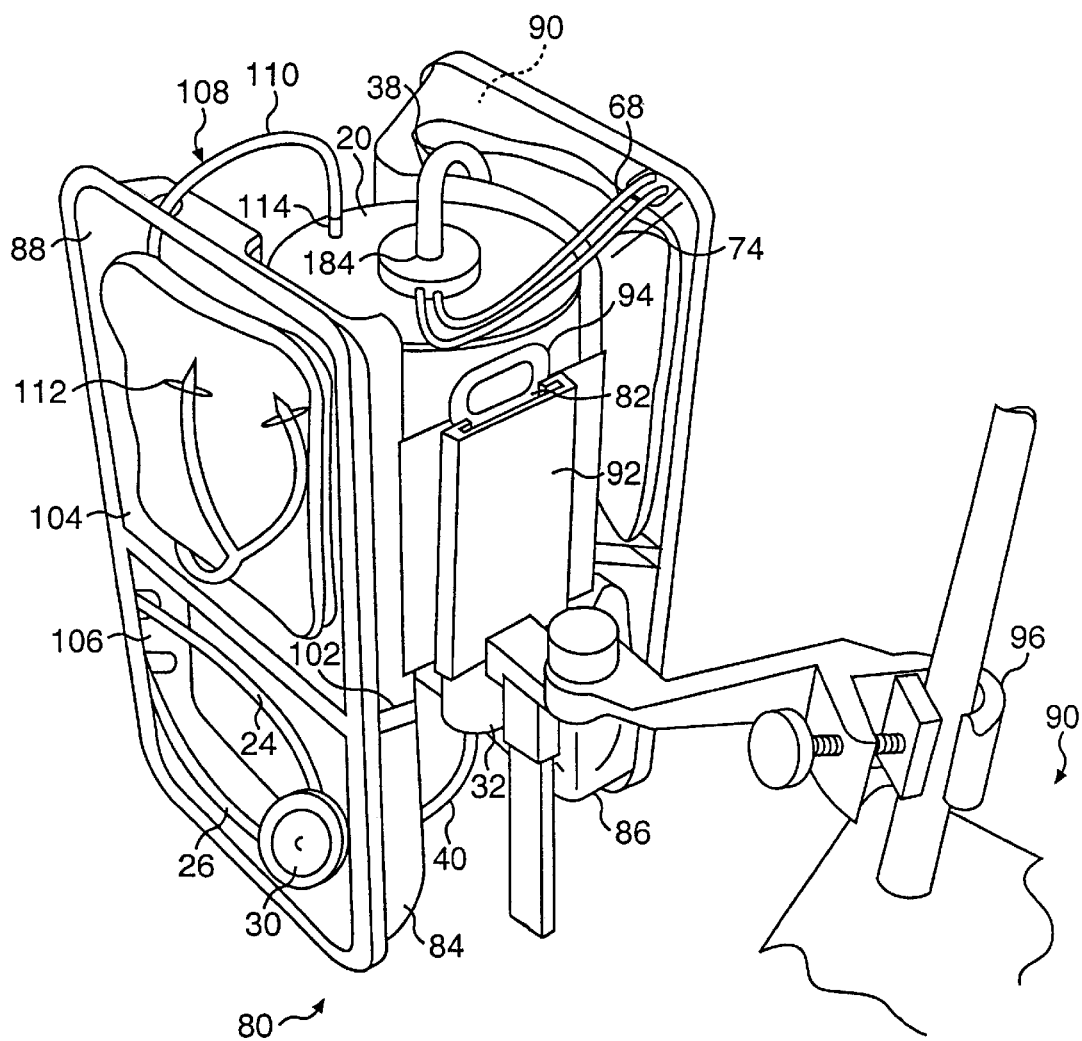
FIG. 2 is a perspective view of a preferred embodiment of the assembly pack of the invention in an undeployed configuration.
Figure 3:
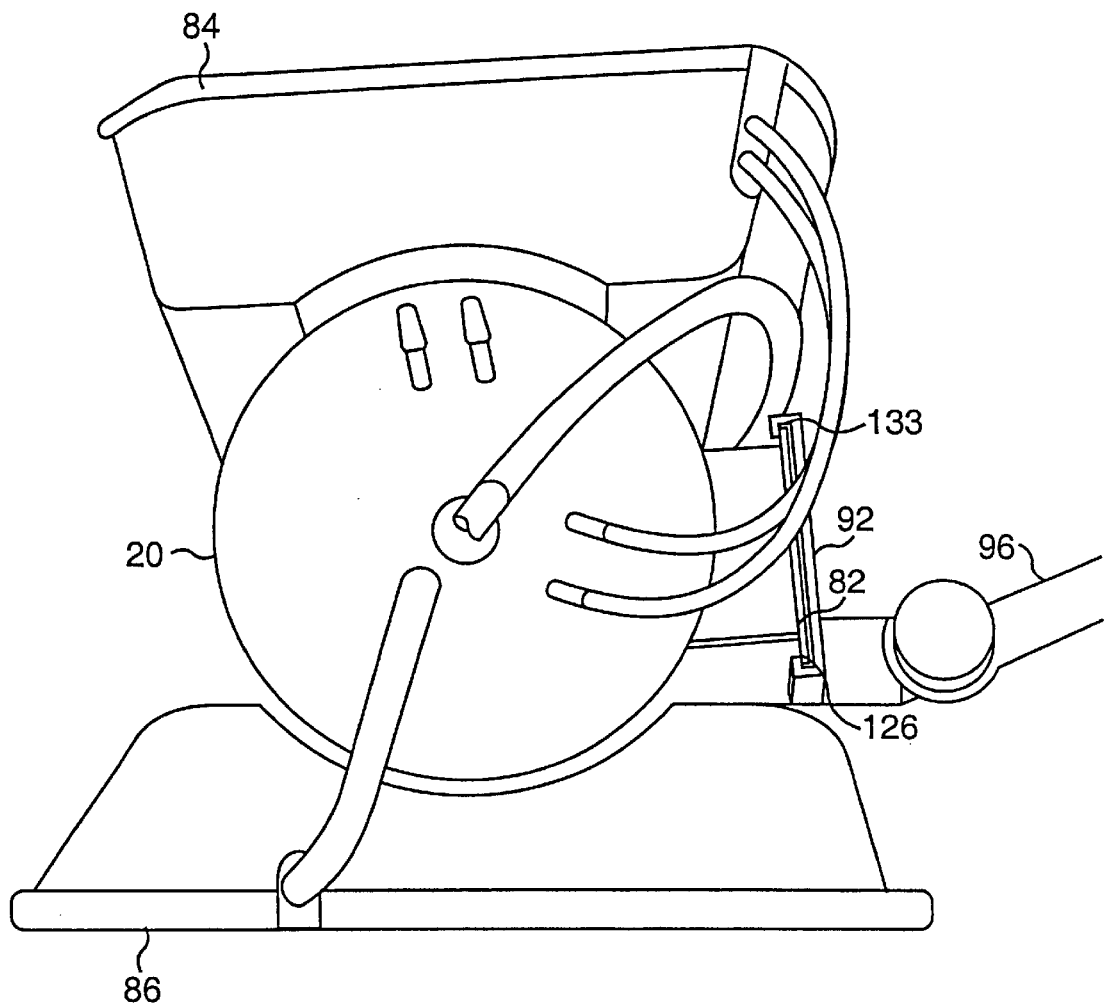
FIG. 3 is a top view of the assembly pack shown in FIG. 2.
Figure 4:
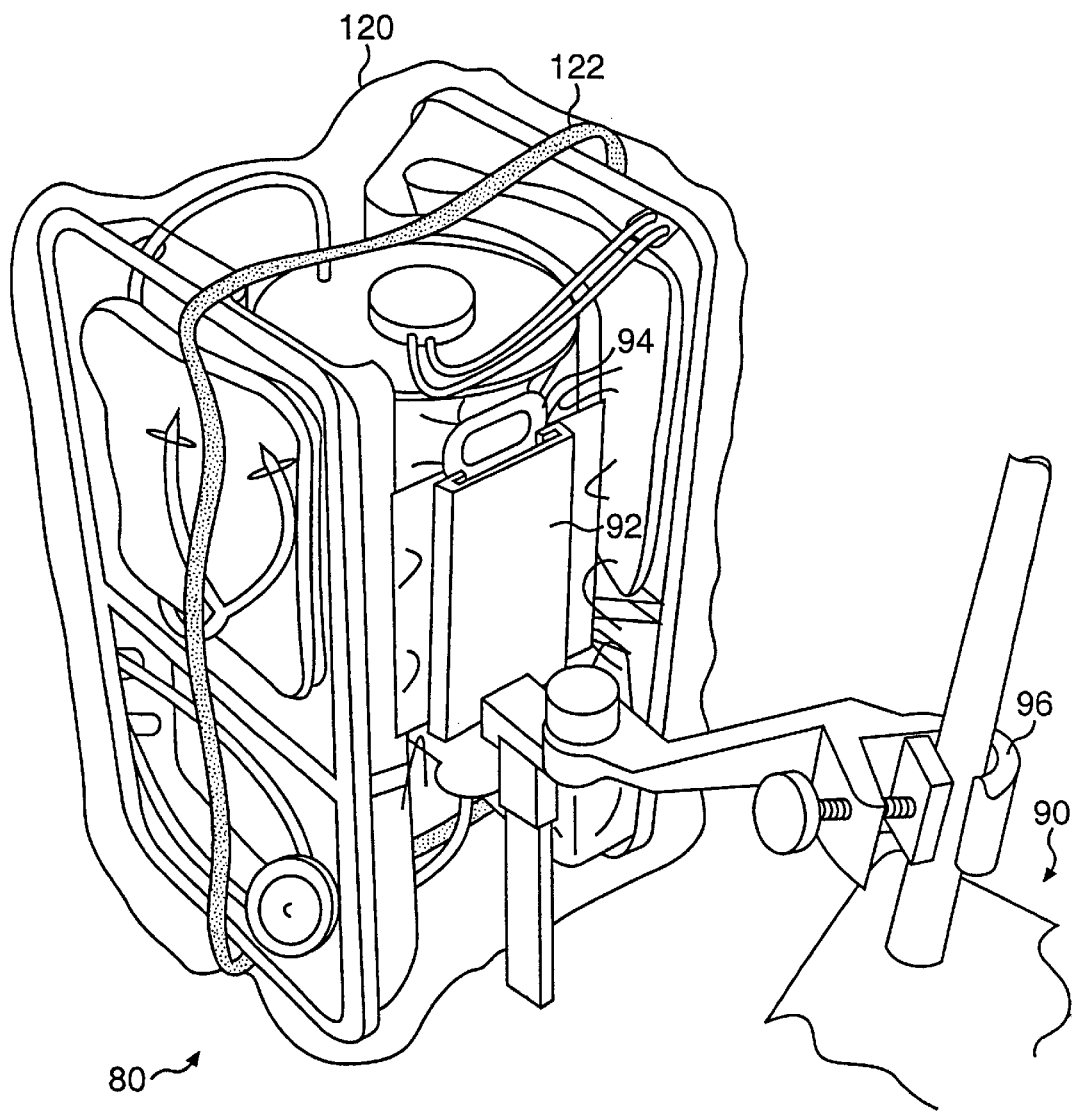
FIG. 4 is a perspective view of an alternative preferred embodiment of the assembly pack of the invention in an undeployed configuration.

The undeployed configuration of a preferred embodiment of the pack assembly 80 is best shown in FIGS. 2–4. A blood reservoir 20 and a blood oxygenator 32 are vertically mounted on carrier 82 with the blood reservoir 20 positioned on top of the blood oxygenator 32. The carrier 82 includes a handle 94 for lifting and repositioning the pack assembly 80, and also includes two vertical flanges 126 that may be slidingly engaged in channel 133 of the mounting bracket 92. Clamp 96 attaches the mounting bracket 92 to a stand assembly 90 and vertically suspends the pack assembly 80 at a height selected by the operator for use during a surgical procedure. In the preferred embodiment, the stand assembly includes the vertical mast of a heart lung machine. However, the pack assembly may optionally be attached to any vertical support structure at a selected height, such as for example a bench or ledge.

The pack assembly 80 preferably also includes two trays 84, 86 which are most preferably attached to the carrier 82. The trays 84, 86 may be attached by hook and loop fasteners, by an adhesive or by any means known to those in the art. Although attachment to the carrier 82 is most preferred, the trays may alternatively be attached to either the reservoir 20 or the oxygenator 32. The trays 84, 86 are sized and shaped to partially enclose the reservoir 20 and oxygenator 32, and are preferably each divided into at least two compartments for holding individual subsystems or coiled lines until needed for use. The trays preferably have cut-out portions through which one end of a stored line may extended for attachment to another component in the system. The cutout portions may be lined with grommets in order to provide a better seal between the tray and the tubing and maintain the sterility of the tray.

As shown in FIG. 2, first tray 84 is divided by partition 102 into an upper compartment 104 and a lower compartment 106. A cover sheet 88 is sealed over the opening of the tray to maintain sterility and to prevent the tray's contents from spilling out of the tray before the pack assembly 80 is deployed for use.

The upper compartment 104 contains a priming line 108 that includes a pair of bag spikes 112 and a priming tube 110 that extends through a cut-out portion of the tray 84 and attaches to the reservoir 20 at prime port 114. When the pack assembly is deployed for use, the prime line 110 will deliver saline solution to the reservoir to prime the system. The lower compartment 106 contains a pump loop including a pump inlet line 24, a pump outlet line 26 and a pump header 30. The pump lines 24, 26 extend through cutouts and attach to the reservoir 20 or oxygenator 32.

The second tray 86 preferably also includes at least two compartments. One of the compartments may include an A-V loop, including a venous line 38 and an arterial line 40, shown in FIGS. 8 and 9. Portions of the venous line 38 and arterial line 40 are preferably extended through cut-outs in the tray compartments to attach to other components in the system. The other compartment of the second tray 86 preferably includes a suction line, such as suction lines 152 and 154, shown in FIGS. 8–9, a portion of which is extended through a cut-out portion of the tray and attached to the reservoir 20.

The cover sheet 88 for the trays 84, 86 is preferably made of a flexible polymeric material, and most preferably of a transparent flexible polymeric material that allows a person who is deploying the circuit to see which components are in the compartments before removing the cover material. The cover sheet 88 may be attached to the trays 84, 86 by an adhesive, by heat sealing or by any method known in the art for sealing a polymeric material to another surface.

As best shown in FIG. 4, the pack assembly 80 may also include a barrier pouch 120 that completely encloses the blood reservoir 20, the blood oxygenater 32 and the carrier 82. The barrier pouch 120 serves to maintain the sterility of the components of the pack assembly. In the preferred embodiment, the pack assembly may be attached or detached from the mounting bracket 92 without removing the barrier pouch 120. The barrier pouch may be constructed of two pieces joined together by sealing strip 122, which facilitates easy removal of the barrier pouch when the pack assembly 80 is needed for use. The barrier pouch is preferably made of a flexible polymeric material, and most preferably is made of a transparent flexible polymeric material. The sealing strip 122 may include hook and loop fasteners, a layer of adhesive or any means known by those in the art for joining together pieces of polymeric sheet material.

The pack assembly 80 has so far been described with reference to an embodiment that includes two trays. However, the pack assembly may include any number of trays that is reasonable given the size and shape of the reservoir and oxygenator, and all such variations are considered to be within the scope of the invention. For example, in one embodiment, separate trays may be provided instead of separate compartments in a larger tray, which may double or triple the number of trays used in the pack assembly. In another embodiment, trays may be placed on the top and bottom of the pack assembly 80 in addition to the trays on the side or sides of the pack assembly 80. Given the possible combinations suggested by the invention, the pack assembly of the invention may include as many as 10 or more trays.

Figure 7:
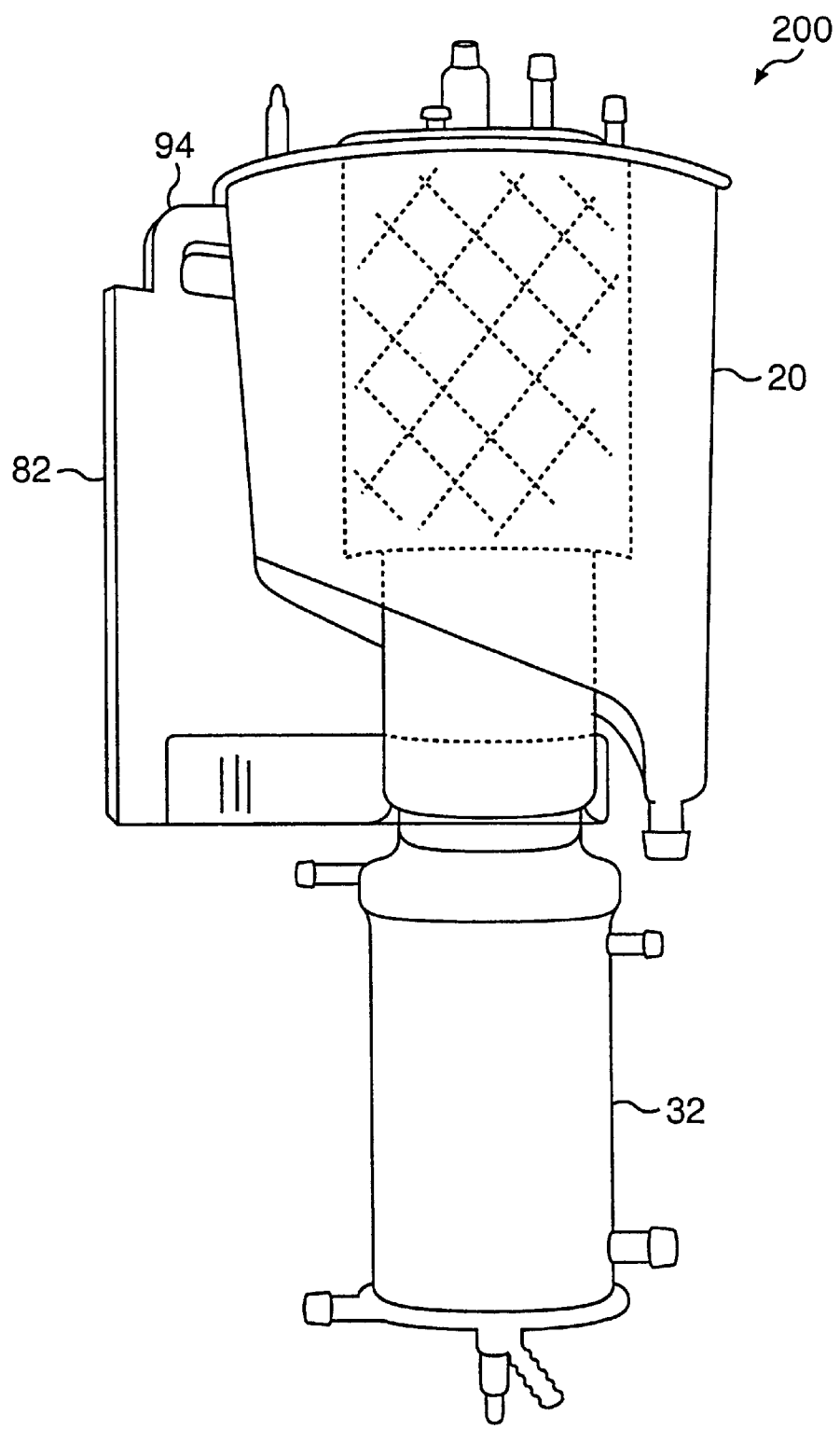
FIG. 7 is a side view of a preferred embodiment of the assembly pack of the invention.

The invention also provides an embodiment that does not include any trays, best shown in FIG. 7. Pack assembly 200 includes the carrier 82, the blood reservoir 20 and the blood oxygenator 32. Even without the trays and associated tubing systems, this embodiment provides an advantage in that it allows the blood reservoir 20 and blood oxygenator 32 to be vertically mounted and easily moved during surgery.

Figure 5:
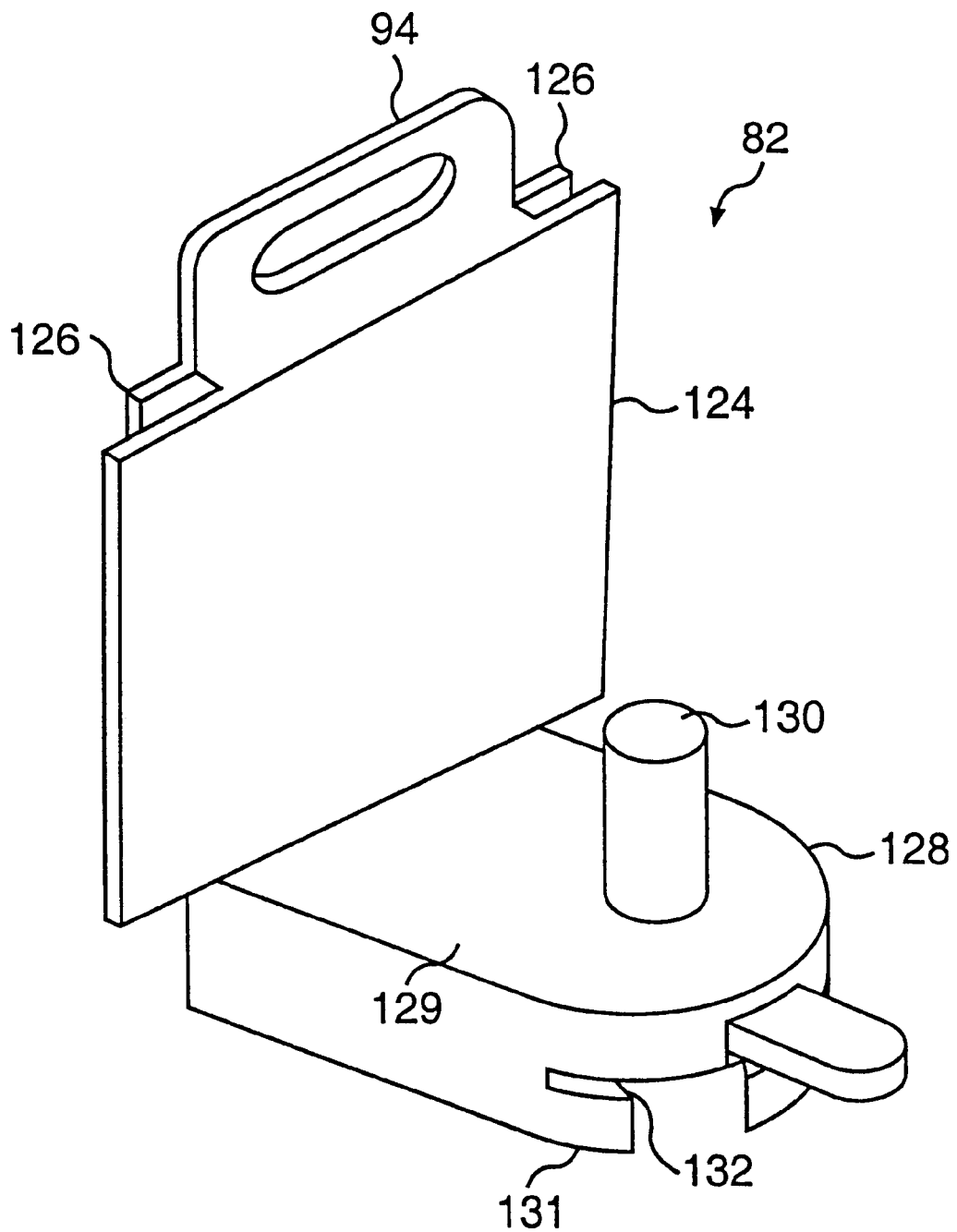
FIG. 5 is a perspective view of the carrier 82 shown in FIGS. 2–4.
Figure 6:
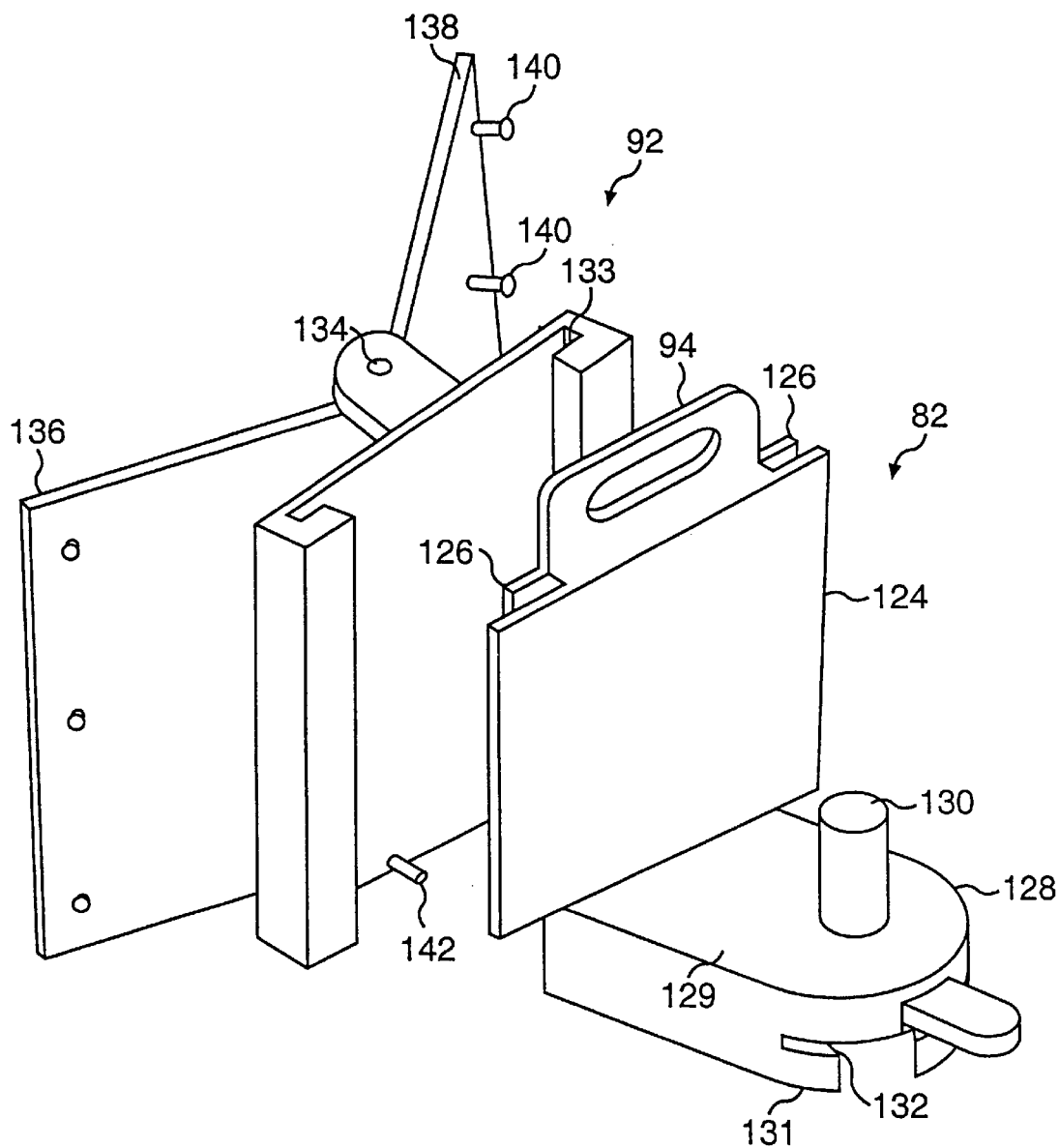
FIG. 6 is a perspective view of the carrier 82 and the mounting bracket 92 shown in FIGS. 2–4.

The structural detail of the carrier 82 and the mounting bracket 92 used in the pack assembly 80 are best shown in FIGS. 5–6. The carrier 82 includes a substantially horizontal attachment plate 128 and a substantially vertical mounting plate 124. These plates may be separately made pieces that are joined together, or more preferably may be parts of a single molded piece. The attachment plate 128 is adapted to support one blood handling apparatus on its top surface 129 and to suspend another blood handling apparatus from its bottom surface 131. The blood handling apparatus supported on the top surface 129 is preferably a blood reservoir or a blood oxygenator, and most preferably is a blood reservoir. The blood handling apparatus suspended from the bottom surface 131 is preferably a blood reservoir or a blood oxygenator, and most preferably is a blood oxygenator.

Each of the two blood handling apparatuses supported by carrier 82 may be separately and independently added or removed from the carrier without disturbing the other blood handling apparatus from the carrier. For instance, if it becomes necessary to replace a blood reservoir 20 during surgery, it may be removed from the carrier 82 without removing the blood oxygenator 32. A blood oxygenator 32 may also be removed from the carrier 82 without removing the blood reservoir 20.

The top surface 129 of the attachment plate 128 preferably includes a retention peg 130 that is sized and shaped to fit into a mating recessed portion in the bottom of a blood reservoir and thereby hold it securely in place. The retention peg 130 is suitable for use with hard bodied blood reservoirs, such as reservoirs that combine the functions of cariotomy blood filtration and venous blood reservoir. However, the retention peg may be advantageously removed when a soft blood reservoir bag is used in the system. In addition to the retention peg, or as an alternative to it, the reservoir may be held in place by a hoop shaped clamp attached to the vertical mounting plate 124. The lower surface 131 of attachment plate 128 includes a channel 132 for receiving and securely retaining a disk attached by a stem to a blood handling apparatus. In the preferred embodiment, the blood handling apparatus is a blood oxygenator and the channel-disk attachment apparatus of attachment plate 128 is the apparatus described in commonly assigned U.S. application Ser. No. 08/962,360, now U.S. Pat. No. 5,958,338, which is incorporated herein by reference.

The vertical mounting plate 124 of the carrier 82 includes a handle 94 and flanges 126 adapted to be slidingly engaged by the slotted track 133 on the mounting bracket 92. To attach the carrier 82 to the mounting bracket 92, the carrier 82 is lifted by the handle 94, and the flanges 126 are guided into the slotted track 133. In a preferred embodiment, the slotted track 133 includes a retention pin 142 to secure the carrier 82 in the track 133. In an alternative preferred embodiment, the track may be tapered so that it is narrower at the bottom than at the top, and the retention pin 142 may be eliminated.

Figure 8:
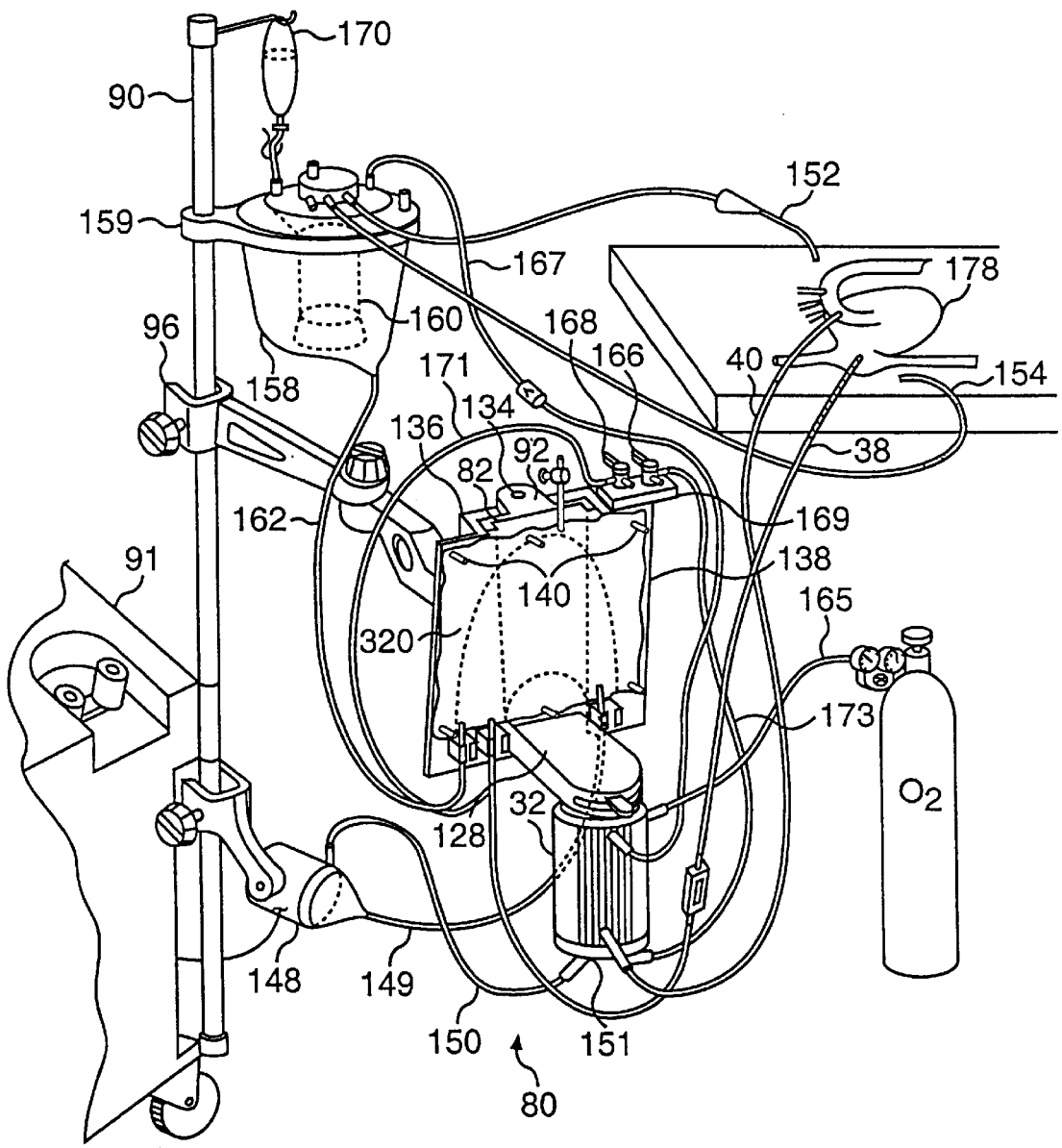
FIG. 8 is a perspective view of a preferred embodiment of the assembly pack of the invention in a deployed configuration.

In an alternative embodiment useful for mounting soft reservoir bags, the mounting bracket 92 includes two panels 136, 138 pivotally mounted on a vertical hinge 134. The panels 136, 138 include pegs or clamps 140 for securing a soft reservoir bag in place, and may be pivoted into a position in which they overlay and are in line with the vertical mounting plate 124 of the carrier 82. In this position the panels 136, 138 may securely suspend a reservoir bag for use. FIG. 8 shows a reservoir bag 320 attached to pivoting panels 136, 138. In addition to hardware for securing a reservoir bag, the panels 136, 138 may also be fitted with an apparatus for controlling the volume of blood in a reservoir bag, such as the apparatus described in commonly assigned U.S. application Ser. No. 09/079,046, which is incorporated herein by reference. The hinge 134 may optionally include only one pivotally mounted door. In other embodiments the hinge 134 may be oriented horizontally instead of vertically.

When a soft reservoir bag is used, the pack assembly 80 will also include a hard shelled cardiotomy reservoir. In the undeployed configuration of this embodiment, the cardiotomy reservoir is secured on top of attachment plate 128 and the soft reservoir bag is preferably folded and retained between the cardiotomy reservoir and the vertical mounting plate 124.

FIG. 8 shows an embodiment of the pack assembly 80 with a soft reservoir 320 and a separate cardiotomy reservoir 158 deployed for use as part of an extracorporeal support circuit. In preparation of the pack assembly 80 for use in a surgical procedure, the components are positioned where necessary in the operating room. The carrier 82 with attached reservoir 320 and oxygenator 32 is attached to the mounting bracket 92. In this embodiment, the mounting bracket includes hinge 134 and panels 136 and 138 with clamps for securing the soft reservoir bag 320. The mounting bracket 92 is attached by clamp 96 to mast 90 of the heart-lung machine 91 at a selected height. The cardiotomy reservoir 158 is removed from the top surface of the attachment plate 128 and elevated above the blood reservoir by a hoop clamp 159 attached to the mast 90.

In use, the extracorporeal circuit of FIG. 8 is primed with saline solution from prime bag 170 before beginning the bypass procedure. After priming, deoxygenated blood is carried from the heart 178 to blood reservoir 320 by venous line 38. The venous blood is then drained from the reservoir 320 by line 149 and delivered by centrifugal pump 148 through line 150 to the oxygenator inlet port 151, where it is oxygenated and returned to the aorta by arterial line 40. Sucker lines 152, 154 collect cardiotomy blood from the incision site and deliver it to the cardiotomy reservoir 158. The cardiotomy blood is passed through a cardiotomy filter 160 and drained by cardiotomy outlet line 162 to the blood reservoir 320 where it is pooled with the venous blood for oxygenation with oxygen delivered by oxygen line 165. Excess air from the oxygenator 32 is vented by vent line 167 to the cardiotomy reservoir 158. A sampling manifold 169 is provided on the carrier 82 for monitoring the quality of blood in the system. Line 173 delivers oxygenated blood to arterial sampling port 166, and line 171 delivers venous blood to venous sampling port 168, for sampling and analysis.

Figure 9:
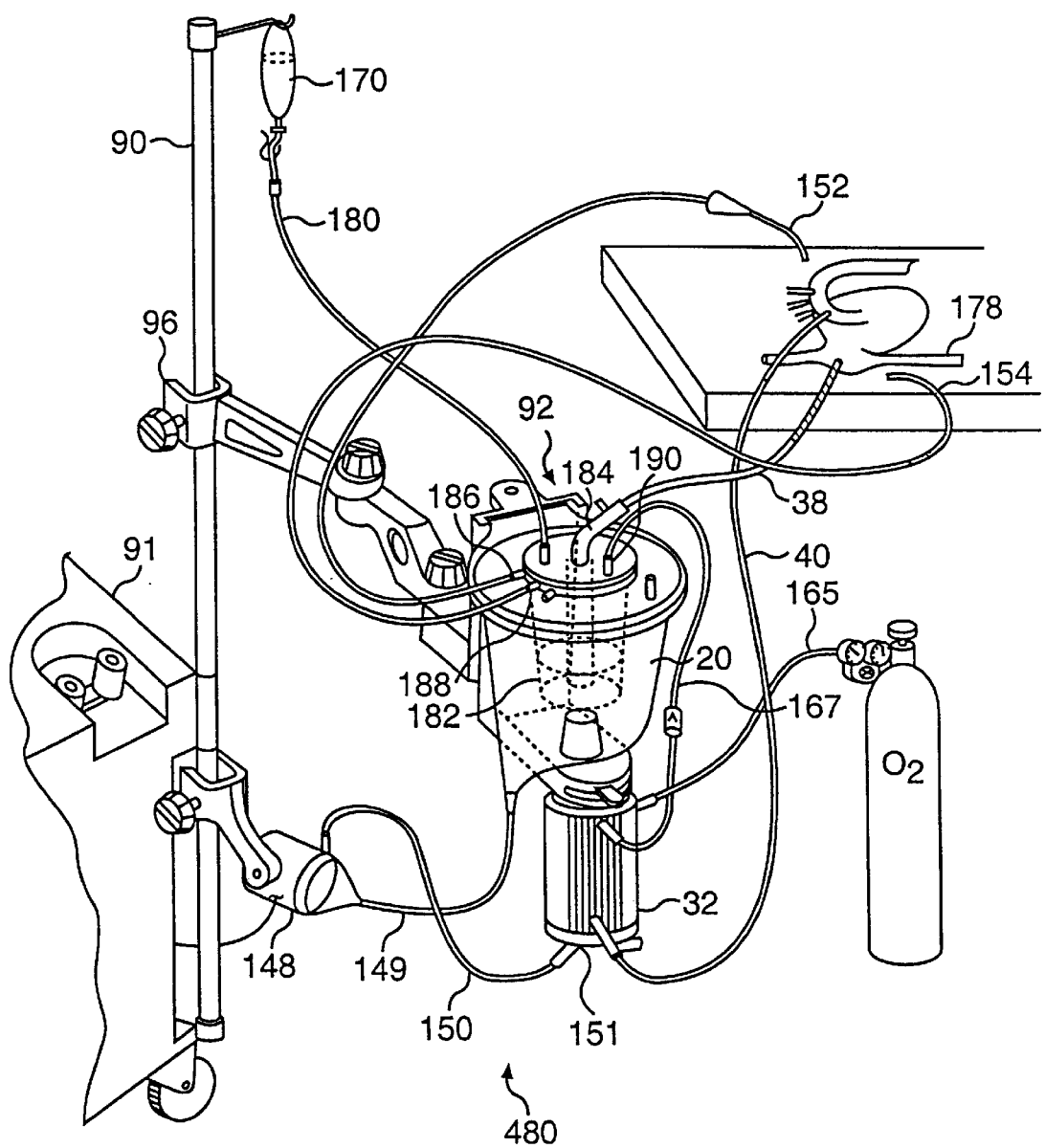
FIG. 9 is a perspective view of an alternative preferred embodiment of the assembly pack of the invention in a deployed configuration.

FIG. 9 shows an alternative embodiment of the pack assembly 480 deployed for use as part of an extracorporeal support circuit. In this embodiment, a single hardshelled reservoir 20 is used that combines the venous reservoir and cardiotomy filter functions in one unit. The pack assembly 80 is deployed for use substantially as described above, except that a separate cardiotomy reservoir is not required and the mounting bracket 92 preferably does not include hinge 134 or doors 136 and 138. In use, the extracorporel circuit is primed with saline solution delivered from prime bag 170 to the blood reservoir 20 by priming line 180. Deoxygenated venous blood is delivered to reservoir inlet port 184 by venous line 38 and pooled in the reservoir 20. The venous blood is then drained by line 149 and pumped by centrifugal pump 148 through line 150 to the oxygenator 32, where it is oxygenated by oxygen supplied through line 165. The oxygenated blood is then returned to the aorta through arterial line 40. Cardiotomy blood scavenged by suckers 152, 154 is delivered to cardiotomy ports 186, 188 and passed through cardiotomy filter 182 before being pooled with venous blood for oxygenation. Recirculation line 167 vents gas from the oxygenator 32 to port 190 on the blood reservoir 20.

The present invention has now been described with reference to several embodiments thereof. The foregoing detailed description has been given for clarity and understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures.

What is claimed is:

1. A pack assembly for use in an extracorporeal blood circuit, comprising:
   (a) a carrier adapted to mount a blood reservoir and a blood oxygenator, said carrier including first and second carrier mounting elements for securely mounting said blood reservoir and said blood oxygenator;
   (b) a blood reservoir releasably secured to the carrier, said blood reservoir including a reservoir mounting element cooperable with one of said carrier mounting elements for securely mounting said blood reservoir to said carrier;
   (c) a blood oxygenator releasably secured to the carrier, said blood oxygenator including an oxygenator mounting element cooperable with one of said carrier mounting elements for securely mounting said blood oxygenator to said carrier; and
   (d) at least one tray releasably attached to at least one of the carrier, the blood reservoir and the blood oxygenator, said at least one tray providing a protective packaging for said blood reservoir and said blood oxygenator and a containment area for tubing components.

2. A pack assembly according to claim 1, further comprising:
   (d) a barrier pouch enclosing the carrier, the blood reservoir and the blood oxygenator.

3. A pack assembly according to claim 1, further comprising:
   (d) a mounting bracket releasably engaged to the carrier.

4. A pack assembly according to claim 3, further comprising:
   (e) a vertical support structure;
   (f) a clamp attaching the mounting bracket to the vertical support structure.

5. A pack assembly according to claim 3, further comprising:
   (e) a hinge associated with the mounting bracket; and
   (f) at least one panel attached to the hinge, the panel including clips or pegs for supporting a blood reservoir.

6. A pack assembly according to claim 1, wherein two trays are releasably attached to the carrier, the blood reservoir or the blood oxygenator.

7. A pack assembly according to claim 1, further comprising:
   (e) a prime line comprising a priming tube and at least one bag spike attached to the reservoir, at least a portion of the prime line being disposed within one of the trays.

8. A pack assembly according to claim 1, further comprising:
   (e) an A-V loop comprising a venous line and an arterial line, at least a portion of the A-V loop being disposed within one of the trays.

9. A pack assembly according to claim 1, further comprising:
   (e) a suction line attached to the reservoir, at least a portion of the suction line being disposed within one of the trays.

10. A pack assembly according to claim 1, further comprising:
    (e) a pump loop comprising a pump inlet line attached to the reservoir, a pump header attached to the pump inlet line, and a pump outlet line attached to the pump header and the oxygenator, the pump header and at least a portion of the pump inlet line and pump outlet line being disposed within one of the trays.

11. A pack assembly according to claim 1, wherein said blood reservoir comprises a cardiotomy reservoir and said pack assembly further comprises a flexible venous blood reservoir mounted on said carrier.

12. A pack assembly according to claim 1, wherein said carrier is adapted to independently and separately mount said blood reservoir and said blood oxygenator such that one of said blood reservoir and said blood oxygenator may be removed from said carrier without removing another of said blood reservoir and said blood oxygenator.

13. A pack assembly according to claim 1, wherein said at least one tray includes a plurality of compartments, each of said plurality of compartments including a predetermined tubing component, and said at least one tray enabling independent and separate deployment of a selected one of said predetermined tubing components.

14. A pack assembly for use in an extracorporeal blood circuit, comprising:
   (a) a carrier adapted to vertically mount a blood reservoir and a blood oxygenator, comprising:
      (i) an attachment plate; and
      (ii) a substantially vertical mounting plate associated with the attachment plate, the mounting plate being adapted for mounting the carrier on a vertical support;
   (b) a blood reservoir releasably attached to the attachment plate; and
   (c) a blood oxygenator releasably attached to the attachment plate;
   wherein the attachment plate of said carrier is adapted to independently and separately mount said blood reservoir and said blood oxygenator such that one of said blood reservoir and said blood oxygenator may be removed from said carrier without removing another of said blood reservoir and said blood oxygenator.

15. A pack assembly according to claim 14, further comprising:
   (d) at least one tray releasably attached to the carrier, the blood reservoir or the blood oxygenator.

16. A pack assembly according to claim 15, wherein two trays are releasably attached to the carrier, the blood reservoir or the blood oxygenator.

17. A pack assembly according to claim 15, wherein the tray is separated into individual compartments.

18. A pack assembly according to claim 15, further comprising:
   (e) a prime line comprising a priming tube and at least one bag spike attached to the reservoir, at least a portion of the prime line being disposed within one of the trays.

19. A pack assembly according to claim 15, further comprising:
   (e) an A-V loop comprising a venous line and an arterial line, at least a portion of the A-V loop being disposed within one of the trays.

20. A pack assembly according to claim 15, further comprising:
   (e) a suction line attached to the reservoir, at least a portion of the suction line being disposed within one of the trays.

21. A pack assembly according to claim 15, further comprising:
   (e) a pump loop comprising a pump inlet line attached to the reservoir, a pump header attached to the pump inlet line, and a pump outlet line attached to the pump header and the oxygenator, the pump header and at least a portion of the pump inlet line and pump outlet lines being disposed within one of the trays.

22. A pack assembly according to claim 14, further comprising:

(d) a barrier pouch enclosing the carrier, the blood reservoir and the blood oxygenator so as to maintain the pack assembly in a sterile condition prior to use.

23. A pack assembly according to claim 14, further comprising:
   (d) a mounting bracket releasably engaged to the mounting plate.

24. A pack assembly according to claim 23, further comprising:
   (e) a vertical support structure; and
   (f) a clamp attaching the mounting bracket to the vertical support structure.

25. A pack assembly according to claim 23, wherein the mounting bracket is adapted to releasably engage the mounting plate without removing the barrier pouch so as to maintain the pack assembly in said sterile condition after mounting said pack assembly on said mounting bracket.

26. A pack assembly according to claim 23, wherein the mounting bracket includes a slotted track capable of slidingly engaging and releasing the mounting plate.

27. A pack assembly according to claim 23, further comprising:
   (e) a hinge associated with the mounting bracket; and
   (f) at least one panel attached to the hinge, the panel including clips or pegs for supporting a blood reservoir.

28. A pack assembly according to claim 27, wherein two panels are attached to the hinge.

29. A pack assembly according to claim 14, wherein the attachment plate has a top surface and a bottom surface, the blood reservoir is supported and retained on the top surface of the attachment plate, and the blood oxygenator is attached to the bottom surface of the attachment plate.

30. A pack assembly according to claim 14, wherein the blood oxygenator includes an attachment disk projecting from its surface on a stem, and the lower surface of the attachment plate has a channel for slidingly engaging and releasing the attachment disk.

31. A pack assembly for use in forming an extracorporeal blood circuit, comprising:
   (a) a carrier adapted to vertically mount a blood reservoir and a blood oxygenator, comprising:
      (i) an attachment plate; and
      (ii) a substantially vertical mounting plate associated with the substantially horizontal attachment plate, the mounting plate being adapted for mounting the carrier on a mast;
   (b) a blood reservoir releasably attached to the attachment plate;
   (c) a blood oxygenator releasably attached to the attachment plate; and
   (d) two trays releasably attached to the carrier, the blood reservoir or the blood oxygenator;
   (e) a prime line comprising a priming tube and at least one bag spike attached to the reservoir, at least a portion of the prime line being disposed within one of the trays;
   (f) an A-V loop comprising a venous line and an arterial line, the venous line attached to the reservoir and the arterial line attached to the oxygenator, at least a portion of the A-V loop being disposed within one of the trays;
   (g) a suction line attached to the reservoir, at least a portion of the suction line being disposed within one of the trays; and
   (h) a pump loop comprising a pump inlet line attached to the reservoir, a pump header attached to the pump inlet line, and a pump outlet line attached to the pump header and the oxygenator, the pump header and at least a portion of the pump inlet line and pump outlet lines being disposed within one of the trays;

wherein said item (a)–(h) are preassembled to define said pack assembly prior to use in an extracorporeal blood circuit.

32. A pack assembly according to claim 31, further comprising:

(i) barrier pouch enclosing elements (a)–(h) of the pack assembly.

33. A pack assembly according to claim 31, further comprising:

(i) a mounting bracket releasably engaged to the mounting plate.

34. A pack assembly according to claim 33, further comprising:

(j) a vertical support structure; and (k) a clamp attaching the mounting bracket to the vertical support structure.

35. A pack assembly according to claim 33, further comprising:

(j) a hinge associated with the mounting bracket; and (k) at least one panel attached to the hinge, the panel including clips or pegs for supporting the supporting a blood reservoir.

36. A pack assembly according to claim 31, wherein said carrier is adapted to independently and separately mount said blood reservoir and said blood oxygenator such that one of said blood reservoir and said blood oxygenator may be removed from said carrier without removing another of said blood reservoir and said blood oxygenator.

* * * * *